United States Patent [19]
Bronner et al.

[11] Patent Number: 6,121,505
[45] Date of Patent: Sep. 19, 2000

[54] PROCESS FOR SYNTHESIZING AND PURIFYING OLEFINS COMPRISING DEHYDROGENATING A PARAFFIN

[75] Inventors: Charles Bronner, Irigny; Reynald Bonneau, Villeurbanne; Pierre Boucot, Ternay; Alain Forestiere, Vernaison, all of France

[73] Assignee: Institut Francais du Petrole, France

[21] Appl. No.: 09/103,524

[22] Filed: Jun. 24, 1998

[30] Foreign Application Priority Data

Jun. 24, 1997 [FR] France .................................. 97 07983

[51] Int. Cl.[7] .......................... C07C 5/327; C07C 5/373; C07C 1/00; C07C 7/00; C10G 9/00
[52] U.S. Cl. .......................... 585/655; 585/324; 585/804; 585/867; 208/101
[58] Field of Search ..................... 585/655, 324, 585/809, 867, 660, 661, 662, 663; 208/101, 100

[56] References Cited

U.S. PATENT DOCUMENTS

| | | | |
|---|---|---|---|
| 4,695,662 | 9/1987 | Vora | 585/324 |
| 5,414,168 | 5/1995 | Scott | 585/2 |

*Primary Examiner*—Marian C. Knode
*Assistant Examiner*—Thuan D. Dang

[57] ABSTRACT

The present invention relates to a process for the production of olefins from a hydrocarbon cut, comprising a step for separating at least one paraffin contained in the hydrocarbon cut, a step for dehydrogenating the paraffin and a step for purifying the hydrogen produced during dehydrogenation, at least a part of that hydrogen being recycled to the dehydrogenation step. The invention is of particular application to the preparation of olefins containing 3 to 5 carbon atoms per molecule from a $C_3$ to $C_5$ hydrocarbon cut containing at least one paraffin.

20 Claims, 1 Drawing Sheet

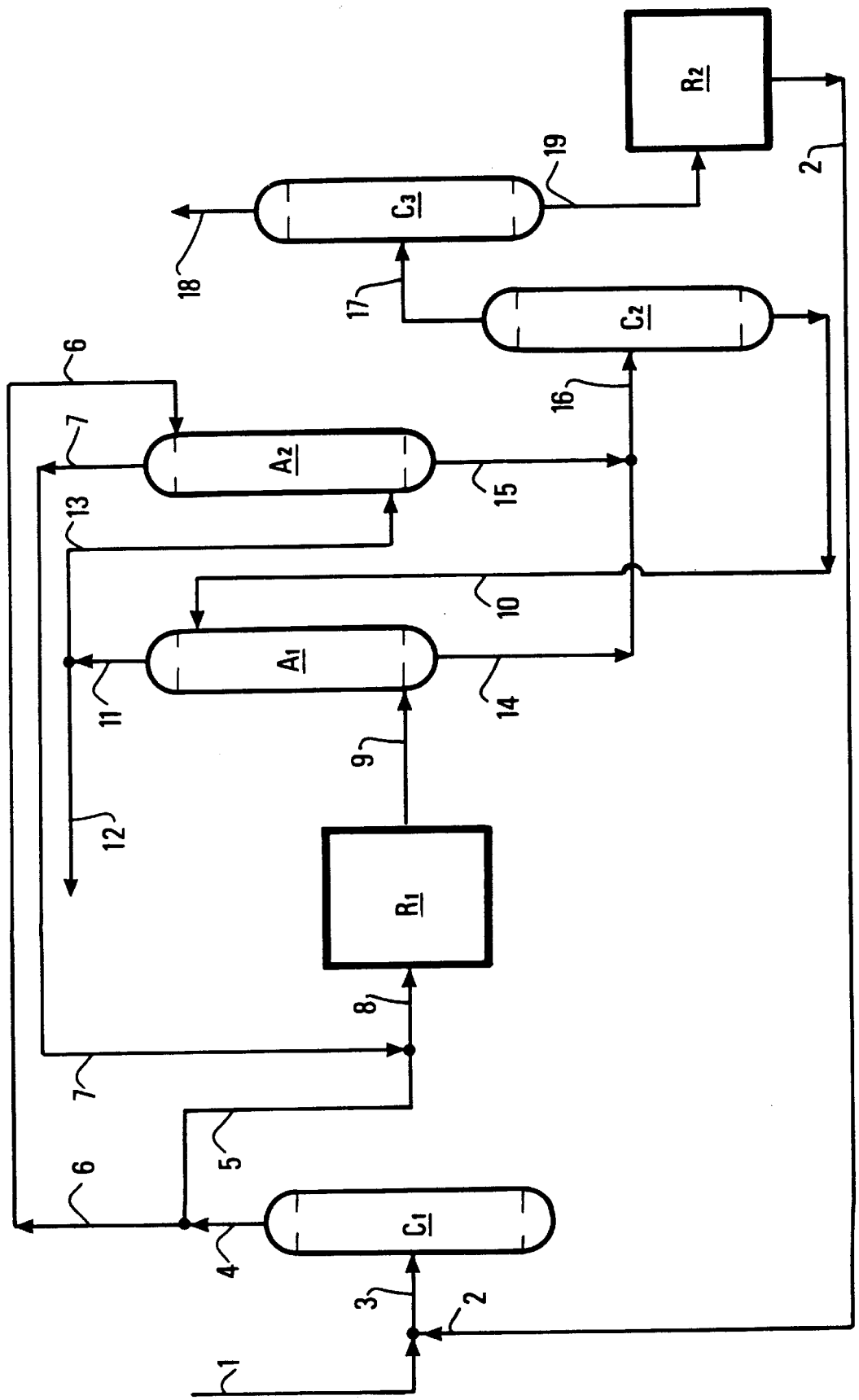

PROCESS FOR SYNTHESIZING AND PURIFYING OLEFINS COMPRISING DEHYDROGENATING A PARAFFIN

The present invention relates to a process for the production of olefins from a hydrocarbon cut, comprising a step for separating at least one paraffin contained in the hydrocarbon cut, a step for dehydrogenating the paraffin and a step for purifying the hydrogen produced during dehydrogenation, at least a part of that hydrogen being recycled to the dehydrogenation step. The invention is of particular application to the preparation of olefins containing 3 to 5 carbon atoms per molecule from a $C_3$ to C5 hydrocarbon cut containing at least one paraffin. It is thus applicable to the production of propene from a $C_3$ cut, to the production of isobutene from a $C_4$ cut and to the production of pentenes (2-methyl-1-butene and/or 2-methyl-2-butene) from $C_5$ cuts.

The remainder of the description relates to the production of isobutene from a $C_4$ cut but should not be considered to be limited to this.

The demand for isobutene has changed greatly in recent years, particularly as a result of the very large demand for MTBE (methyl-tertio-butyl-ether) which itself is connected with that for unleaded gasoline. This demand is thus increasing greatly.

In the United States, the Clean Air Act-has contributed to encouraging the introduction of compounds such as ethanol, MTBE or ETBE (ethyl-tertio-butyl-ether) into gasoline. Such compounds, which until now have been used as high octane number components in unleaded gasoline, have seen the opening up of a new field of application in reformulated gasoline because of their recognised anti-polluting properties. In this context, the demand for MTBE has increased by an amount of more than 15% a year.

Butenes in general and isobutene in particular mainly originate from $C_4$ cuts, either from catalytic cracking, or from steam cracking. The composition of such $C_4$ cuts depends on the type of cracking; they contain 15 mole % to 30 mole % of isobutene when they originate from the steam cracker, and are characterised by high amounts of butadiene (35 mole % to 50 mole %) and low butane contents; after extracting the butadiene, the cut contains 45 mole 5 to 50 mole % of isobutene. Catalytic cracking cuts are distinguished by an almost complete absence of butadiene, by a relatively low isobutene content and by relatively high quantities of isobutane. To a lesser extent, butenes can originate from smaller scale operations, which are very often in captive masses, from isobutane dehydrogenation or from dehydrating t-butyl alcohol in the case of isobutene.

The availability of very pure isobutene is relatively low. The possibilities for the availability of that hydrocarbon are, inter alia, greatly influenced by markets for butadiene. If the latter is not extracted, the whole cut is usually recycled to the steam cracker and isobutene is no longer available.

The availability of isobutene from steam crackers, currently the principal suppliers, will not be sufficient to satisfy such a demand and it will thus be necessary to turn to other sources such as that consisting of dehydrogenating isobutane which can be obtained by isomerising natural butane or from catalytic cracking.

The production of isobutene from isobutane, and more generally the production of an olefin from the corresponding paraffin by dehydrogenation, has been known for a long time. The process consists of converting the paraffin to the corresponding olefin, usually in the presence of a solid catalyst and a diluting gas, at a low pressure and at a high temperature.

The problem with the process lies in recovering the isobutene and unreacted isobutane in liquid form and the gaseous hydrogen formed which must be of high purity for both technical and economic reasons. Hydrogen is a by-product of the reaction which can be used, for example, in the other refinery units, as well as being recycled to the reaction section, a step which is indispensable to the dehydrogenation process for catalyst stability reasons.

At least two methods exist for purifying the hydrogen used as above, which methods have already been described and used on an industrial scale.

The chill group method described, for example, in United States patents U.S. Pat. No. 4,663,493, U.S. Pat. No. 4,381, 417 and U.S. Pat. No. 4,381,418, using what is termed in the art an expander, a turbine supplied with a pressurised fluid which is depressurised and work is recovered. Energy production greatly reduces the temperature of the fluid with partial condensation despite the reduction in pressure. Such condensation enables more isobutene and isobutane to be recovered while increasing the purity of the hydrogen produced and recycled. In order to be able to be used in other hydrotreatment units, the hydrogen produced must be re-compressed to the working pressure. The purification of hydrogen and recovery of isobutane and isobutene using that method are complicated and expensive operations, which in particular involve the use of cryogenic systems which require heavy investment (expensive machines such as expanders) and by the high costs of refrigeration cycles operating at very low temperatures.

The absorption method described, for example, in U.S. Pat. No. 4,695,662, U.S. Pat. No. 4,329,516 and European patent EP-A-0 502 265 use one or more absorption columns. In that method, the gaseous effluent is sent to an absorption column where the isobutene and isobutane are dissolved in an absorbing fluid and subsequently recovered as a liquid distillate from a column, the bottoms from which is chilled and recycled to the absorption column. A second absorption column, with a liquid used or produced in the downstream treatments can possibly produce a higher purity of hydrogen and better recovery. That method is less complex to carry out than the chill group method and requires less investment. The absorption methods described in the three patents cited above are incorporated into MTBE production.

Thus patent application EP-A-0 502 265 describes a process for MTBE synthesis comprising an isobutane dehydrogenation step in which the gaseous effluent from the dehydrogenation zone is sent to an absorption purification zone which uses MTBE as the absorption liquid. The gaseous hydrogen recovered from the absorption zone outlet is not further purified and its possible use in the dehydrogenation zone is not discussed. That method of operating is only applicable when it is incorporated in an MTBE production process. It is not suitable where dehydrogenation is not carried out close to an MTBE production site.

U.S. Pat. No. 4,329,516 describes a process for MTBE synthesis comprising a step for isomerising butane to isobutane, and a step for dehydrogenating isobutane in which the gaseous effluent from the dehydrogenation zone is sent to an absorption purification zone which uses an absorption liquid. The absorption liquid used in that process is not specified. However, it is disclosed that the gaseous mixture from the absorption zone can then be re-treated either by absorption or by chilling to recover hydrogen gas which can then be used in the isomerisation unit or in any other hydrogen-consuming unit such as a hydrocarbon hydrodesulphuration unit, for example. The teaching of that patent regarding purification of the gaseous product from the dehydrogenation zone, and in particular hydrogen, is thus very limited. Further, the teaching of that patent is limited to the case where an isomerisation unit, a dehydrogenation unit and an MTBE synthesis unit are integrated together.

U.S. Pat. No. 4,695,662 describes a process for dehydrogenating light paraffin to olefins, in particular for dehydrogenating isobutane to isobutene particularly for integration into the production of MTBE from the isobutene thus formed. The conversion process comprises a dehydrogenation reaction section. The reaction effluent from the dehydrogenation section is sent to a first counter-current absorber in which it is brought into contact with a hydrocarbon cut $C_5^+$ possibly containing MTBE. From the first absorber, a first vapour phase is obtained which is depleted in hydrogen-containing hydrocarbons, light compounds and $C_5^+$ fractions. That vapour passes through a second counter-current absorption zone with a fluid containing propane and possibly butanes. The purified hydrogen gas from the head of the second absorber is divided into two portions: exported hydrogen production and recycled hydrogen sent to the reaction section. The bottoms products from the two absorption columns are then treated in columns to eliminate light products (de-ethaniser), to recover upgradable products (depropaniser and debutaniser). The absorption fluids exit from the bottom of the debutaniser for the first absorber and liquid distillate from the depropaniser for the second. The liquid distillate from the debutaniser constitutes the feed for the etherification reaction section. In that process, the ensemble of the non absorbed gaseous products in the first absorber is sent to the second absorber, which means that the second absorber must have large dimensions which thus requires a very large quantity of absorption solvent. Further, the use of a hydrocarbon mixture comprising compounds containing three carbon atoms and compounds containing four carbon atoms in the second absorber pollutes the hydrogen recycled to the dehydrogenation section with $C_3$ compounds, which does not encourage proper operation of the unit.

The present invention aims to overcome the disadvantages described above and provide a method for producing olefins by dehydrogenating at least one paraffin to obtain a recyclable hydrogen containing no heavy compounds and an exported hydrogen with sufficient purity for use in hydrogen-consuming units present on the industrial site containing the dehydrogenation unit or on a more remote industrial site.

Hydrogen purification satisfies technical and economic constraints. The exported hydrogen can be used in other hydrotreatment units in a refinery such as units for hydrodesulphuration of cuts from straight run distillation of crude oil. The high purity of the hydrogen is an important economic factor. For hydrogen recycling, clearly purity is also an important economic factor, but purity is also a technical constraint in that heavy hydrocarbons contained in the recycled gas can, for example, promote coke formation during the dehydrogenation reaction but this is not limiting.

The invention enables heavy hydrocarbons to be eliminated from the produced or recycled hydrogen, after initial purification in an absorber using a gasoline fraction, then in a recontacting column to replace the residual heavy hydrocarbons with a fraction of the feed from the dehydrogenation reaction section.

In its broadest scope, the invention can be defined as a process for the production of olefins and hydrogen by dehydrogenation of at least one paraffin, comprising:

a) a step for introducing a hydrocarbon feed comprising at least one paraffin containing at least two carbon atoms into a dehydrogenation reaction zone in the presence of hydrogen kept under dehydrogenation conditions and for producing at least one reaction effluent containing at least one olefin, hydrogen and the unconverted fraction of said feed;

b) a first step for bringing the reaction effluent obtained from step a) into counter-current contact with a heavy hydrocarbon fraction in an absorption zone under absorption conditions and for producing at least one gaseous hydrocarbon fraction containing the majority of the hydrogen initially present in the effluent from step a), a portion of said heavy hydrocarbon fraction, and light hydrocarbon compounds and a liquid hydrocarbon fraction containing the majority of said heavy hydrocarbon fraction, the olefin and the unconverted fraction of said paraffin;

c) a step in which a portion of the gaseous hydrocarbon fraction containing hydrogen separated in step b) is recovered and the other portion of the gaseous hydrocarbon fraction containing hydrogen is sent to a second step for bringing said gaseous hydrocarbon fraction into counter-current contact with a light hydrocarbon fraction in an absorption zone under absorption conditions and for producing at least one gaseous fraction containing the majority of the hydrogen initially present in the gaseous fraction of step b) and the majority of said light hydrocarbon fraction, at least a portion of said gaseous fraction being recycled to dehydrogenation step a), and a liquid hydrocarbon fraction containing a portion of said light hydrocarbon fraction and a portion of said heavy hydrocarbon fraction used in step b) which is recovered;

said process being characterized in that the light hydrocarbon fraction used in step c) is constituted by a portion of the hydrocarbon feed introduced into dehydrogenation step a).

In a particular implementation, the process of the present invention comprises a fractionation step in which the liquid hydrocarbon fractions from steps b) and c) are fractionated to a heavy hydrocarbon fraction at least a portion of which is preferably recycled to step b) and a light hydrocarbon fraction containing the desired olefin and unconverted paraffin from which it is formed, and light compounds. In a preferred implementation, this light hydrocarbon fraction is then fractionated into a fraction containing essentially the desired olefin and unconverted paraffin from which it is formed and to a fraction containing the light compounds which is usually eliminated, for example flared off.

In a particular implementation, the fraction containing essentially the desired olefin and unconverted paraffin from which it is formed is sent to an etherification reaction zone from which an ether is formed which is separated and purified. At least a portion of the unconverted hydrocarbon fraction is preferably recycled to dehydrogenation step a).

In a preferred implementation of the invention, the hydrocarbon feed comprising at least one paraffin containing at least two carbon atoms which is introduced to the dehydrogenation reaction zone is preferably a feed comprising essentially hydrocarbon compounds containing the same number of carbon atoms, and usually it contains essentially the hydrocarbon compound which it is desired to dehydrogenate. Thus in the case of a $C_4$ cut the feed introduced into the dehydrogenation zone will contain essentially isobutane, a very small proportion of n-butane and practically no or a very small amount of hydrocarbons containing 3 or 5 carbon atoms per molecule.

When the feed comprises a plurality of hydrocarbons containing a variable number of carbon atoms, it is preferably to provide, prior to the dehydrogenation zone, a fractionation zone from which said feed is split, for example, into a homogeneous fraction comprising hydrocarbons containing the same number of carbon atoms which is sent to the dehydrogenation zone, and into a heavier fraction which is recovered for other uses. As an example, in the case of a $C_4$ cut, it is fractionated, for example by distillation, into a fraction comprising essentially compounds containing 4 carbon atoms per molecule and into a heavier product comprising compounds containing at least 5 carbon atoms per molecule. In the case of dehydrogenation of isobutane, the heavy hydrocarbon feed used in the first absorption zone is, for example, a naphtha or a $C_5-C_7$ gasoline.

The dehydrogenation reaction is usually carried out in the presence of a conventional catalyst which is well known to the skilled person. This is also the case for the operating conditions for this reaction which are conventional conditions which are well known to the skilled person and have been widely described in the literature, generally associated with the catalyst used and with the hydrocarbon compound which is to be dehydrogenated. In the case of dehydrogenating a $C_4$ cut containing essentially isobutane to produce isobutene, the temperature is normally about 400° C. to 800° C., usually about 500° C. to 700° C., the pressure is normally about 0.05 MPa to about 5 MPa, and the space velocity defined as the quantity of feed introduced per hour with respect to the quantity of catalyst (WHSV) is about 0.05 to about 20, usually about 0.5 to 5. The ratio of hydrogen to hydrocarbons is normally about 0.01 to about 10, usually about 0.1 to about 2. The catalyst used is usually a catalyst containing platinum on an alumina support. The platinum content is generally about 0.01% to about 5% by weight, usually about 0.1% to about 2% by weight.

The absorption conditions are conventional conditions which are well known to the skilled person. The absorption columns are normally conventional columns. The general conditions prevailing in the absorption columns in the case of treating a $C_4$ cut are a pressure which is usually above atmospheric pressure and below about 6 MPa, although a higher pressure could be envisaged. This pressure is usually about 0.05 to about 1.5 MPa. The temperature in the first absorption zone when treating a $C_4$ cut is normally below about 160° C. and usually below about 100° C. this temperature is normally over 10° C. and usually over 20° C. The hourly space velocity (HSV) is normally about 0.1 to about 10 h$^{-1}$, usually about 0.2 to about 5 $^{-1}$. The number of plates is normally about 9 to about 50, usually about 10 to about 30.

The pressure in the second absorption zone is in the same range as that prevailing in the first absorption zone, but in contrast the temperature is normally lower. This temperature in the case of treating a $C_4$ cut is normally below about 100° C., usually below about 10° C. This temperature is normally over −80° C. and usually over −30° C. In this second zone, the hourly space velocity (HSV) is normally in the same range as that used in the first absorption zone. The number of plates is normally below the number of plates existing in the first zone. It is normally about 1 to about 30 and usually about 2 to about 20.

The single FIGURE is a schematic illustration of the process of the present invention. The description of this FIGURE is given for dehydrogenating isobutane obtained from a $C_4$ cut but this is in no way limiting. The cut containing isobutane is mixed in line L1 with a recycle from line L2 from the downstream etherification, purification and hydrogenation section. This mixture is introduced into a distillation column C1 (deisobutaniser) via line L3 to produce a very pure isobutane cut overhead via line L4. This feed is divided into two streams. The major stream is mixed in line L5 with recycled hydrogen arriving via line L7. This mixture is sent via line L8 to reaction section R1. This mixture constitutes the feed to the dehydrogenation reaction section R1. The minor stream is sent via line L6 to a re-contacting column (second absorption zone) (recontacter) and its use will be described below. The effluent from the reaction section, after compression and chilling, is sent via line L9 to the bottom of absorption column A1 (absorber) while the absorbing fluid is sent to the head of the column via line L10. The overhead vapour from the absorber which leaves via line L11 is divided into two streams. The first stream is recovered via line L12 and constitutes the hydrogen exported to other hydrotreatment units, while the second stream is sent via line L13 to recontacting column A2. This hydrogen is intended to be recycled to dehydrogenation reaction section R1, after removing the heavy fractions. The hydrogen from absorber A1 via line L13 is introduced to the bottom of column A2, while the isobutane fraction of the feed is introduced to the head of column A2 via line L6. In the presence of hydrogen, the isobutane vaporises and causes chilling. Under the effect of the chilling, the heavy hydrocarbons still present in the gas condense out. In the gas produced from the head of recontacter A2, the heavy hydrocarbons are replaced by isobutane which is then sent to reaction section R1 via line L7, mixed with hydrogen thus purified. This mixture thus constitutes a portion of the feed for the isobutane dehydrogenation unit. The product from the bottom of absorber A2 is sent via line L15 to line L16 in which it is mixed with the bottoms product from recontacter A1 arriving via line L14, then the mixture is sent via line L16 to debutanisation column C2 from which the liquid distillate is sent to depropaniser C3 via line L17 and the bottoms product is sent to the head of absorber A1 via line L10. The overhead product from the depropaniser which leaves via line L18 is constituted by light fractions sent to the combustible gas transmission system while the bottoms product which leaves via line L19 represents the supply to the etherification, purification and hydrogenation section R2.

The following example illustrates the invention more precisely for the production of isobutene by dehydrogenation of isobutane. It is not limiting.

EXAMPLE 1

A feed in a proportion of 78.96 kilomoles per hour (kmol/h) containing 97.67% of isobutane, 0.99% of n-butane, 1.33% of propane and 0.01% of isobutene was introduced into the dehydrogenation zone comprising 4 reactors in series. The catalyst used in the reactors was a commercial catalyst containing 0.6% by weight of platinum on a cubic gamma alumina with a specific surface area of 200 m$^2$/g in the form of 1.8 millimeter diameter beads. The unit comprised heating means upstream of each reactor. The average temperature in the reactors was 580° C., the absolute pressure at the inlet to the first reactor was 0.3 MPa and it was 0.15 MPa at the outlet from the last reactor, the WHSV was 2 and the $H_2$/hydrocarbons molar ratio was 0.5. The material balances are given in Table 1 below. The balances for the absorbers were calculated using software sold by the American company SIMSCI (SIMulation SCIence INC.) under the trade name Pro 11.

TABLE 1

| BALANCE in kmol/h | Absorber head A1 line L11 | Exported hydrogen line L12 | Hydrogen to contacter A2 line L13 | Isobutane to contacter A2 line L6 | Bottom of contacter A2 line L15 | Recycled hydrogen line L7 |
|---|---|---|---|---|---|---|
| Hydrogen | 1548.44 | 689.14 | 859.30 | 0 | 0.25 | 859.05 |
| Methane | 28.96 | 12.89 | 16.07 | 0 | 0.06 | 16.02 |
| $C_2 + C_3$ | 3.92 | 1.75 | 2.17 | 1.03 | 0.18 | 3.03 |
| Isobutane | 7.61 | 3.39 | 4.22 | 77.12 | 8.03 | 73.32 |
| n-butane | 1.21 | 0.54 | 0.67 | 0.78 | 0.54 | 0.92 |
| 1-butene | 0.52 | 0.23 | 0.29 | 0 | 0.14 | 0.16 |
| Isobutene | 5.52 | 2.46 | 3.06 | 0.01 | 1.39 | 1.68 |
| $C_5 + C_6$ | 23.47 | 10.44 | 13.03 | 0 | 12.67 | 0.35 |
| TOTAL (kmol/h) | 1619.65 | 720.84 | 898.81 | 78.94 | 23.26 | 954.53 |

The purity of the recycled hydrogen was inferior to that of the exported hydrogen but the amount of the heavier than butane fraction was lower and it contained isobutane which was the product which was to be dehydrogenated. Thus apart from the isobutane, the purity of the recycled hydrogen was much higher than that of the exported hydrogen. The exported fraction (line L12) contained 95.6 mole % of hydrogen and 1.44 mole % of $C_5$ and $C_5^+$hydrocarbon fraction. The recycled fraction (line L7) contained 90 mole % of hydrogen and only 0.04 mole % of $C_5$ and $C_5^+$hydrocarbon fraction. Apart from the isobutane, the purity of this fraction was much higher since it was 97.5 mole %.

What is claimed is:

1. A process for the production of olefins and hydrogen by dehydrogenation of at least one paraffin, comprising providing a hydrocarbon feed and:

a) introducing a first fraction of said hydrocarbon feed comprising at least one paraffin containing at least two carbon atoms into a dehydrogenation reaction zone in the presence of hydrogen kept under dehydrogenation conditions to produce at least one reaction effluent containing at least one olefin, hydrogen and an unconverted fraction of said feed;

b) bringing the reaction effluent obtained from step a) into counter-current contact with a heavy hydrocarbon fraction in an absorption zone under absorption conditions to produce at least one first gaseous hydrocarbon fraction and a first liquid hydrocarbon fraction, wherein the first gaseous hydrocarbon fraction comprises the majority of the hydrogen initially present in the effluent from step a), a portion of said heavy hydrocarbon fraction, and light hydrocarbon compounds, and wherein the first liquid hydrocarbon fraction comprises the majority of said heavy hydrocarbon fraction, the olefin and the unconverted fraction of said paraffin;

c) recovering a first portion of the first gaseous hydrocarbon fraction containing hydrogen separated in step b) and sending a second portion of the first gaseous hydrocarbon fraction containing hydrogen to a second step comprising bringing said second portion into counter-current contact with a light hydrocarbon fraction in an absorption zone under absorption conditions to produce at least one second gaseous fraction and a second liquid hydrocarbon fraction, wherein the second gaseous fraction comprises the majority of the hydrogen initially present in the gaseous fraction of step b) and the majority of said light hydrocarbon fraction; recycling at least a portion of said second gaseous fraction to dehydrogenation step a), wherein said second liquid hydrocarbon fraction comprises a portion of said light hydrocarbon fraction and a portion of said heavy hydrocarbon fraction used in step b), and recovering said second liquid hydrocarbon fraction;

wherein the light hydrocarbon fraction used in step c) comprises second fraction of the hydrocarbon feed.

2. A process according to claim 1, comprising a fractionation step d) in which the liquid hydrocarbon fractions from steps b) and c) are fractionated to a heavy hydrocarbon fraction and a light hydrocarbon fraction containing the desired olefin and unconverted paraffin from which it is formed, and light compounds.

3. A process according to claim 2, in which at least a portion of the heavy hydrocarbon fraction obtained in step d) is recycled to step b).

4. A process according to claim 2, in which the light hydrocarbon fraction obtained in step d) is fractionated into a fraction containing essentially the desired olefin and unconverted paraffin from which it is formed and into a fraction containing light compounds.

5. A process according to claim 4, in which the fraction containing essentially the desired olefin and unconverted paraffin from which it is formed is sent to an etherification reaction zone from which an ether is formed.

6. A process according to claim 5, in which at least a portion of the hydrocarbon fraction which is not converted in the etherification step is recycled to dehydrogenation step a).

7. A process according to claim 1, in which the hydrocarbon feed comprising at least one paraffin containing at least two carbon atoms which is introduced into the dehydrogenation reaction zone is a feed comprising essentially hydrocarbon compounds containing the same number of carbon atoms.

8. A process according to claim 1, in which the hydrocarbon feed which is introduced into the dehydrogenation reaction zone contains essentially the hydrocarbon compound which it is desired to dehydrogenate.

9. A process according to claim 1, in which the hydrocarbon feed introduced into the dehydrogenation reaction zone is a $C_4$ cut.

10. A process according to claim 1, comprising a prior fractionation step in which the hydrocarbon feed is split into a homogeneous fraction comprising hydrocarbons containing the same number of carbon atoms which is sent to the dehydrogenation zone and into a heavier fraction which is recovered.

11. A process according to claim 3, wherein the light hydrocarbon fraction obtained in step d) is fractionated into a fraction containing essentially the desired olefin and unconverted paraffin from which it is formed and into a fraction containing light compounds.

12. A process according to claim 2, wherein the hydrocarbon feed comprising at least one paraffin containing at least two carbon atoms which is introduced into the dehydrogenation reaction zone is a feed comprising essentially hydrocarbon compounds containing the same number of carbon atoms.

13. A process according to claim 3, wherein the hydrocarbon feed comprising at least one paraffin containing at least two carbon atoms which is introduced into the dehydrogenation reaction zone is a feed comprising essentially hydrocarbon compounds containing the same number of carbon atoms.

14. A process according to claim 2, wherein the hydrocarbon feed which is introduced into the dehydrogenation reaction zone contains essentially the hydrocarbon compound which it is desired to dehydrogenate.

15. A process according to claim 3, wherein the hydrocarbon feed which is introduced into the dehydrogenation reaction zone contains essentially the hydrocarbon compound which it is desired to dehydrogenate.

16. A process according to claim 2, wherein the hydrocarbon feed introduced into the dehydrogenation reaction zone is a $C_4$ cut.

17. A process according to claim 3, wherein the hydrocarbon feed introduced into the dehydrogenation reaction zone is a $C_4$ cut.

18. A process according to claim 2 comprising a prior fractionation step wherein the hydrocarbon feed is split into a homogeneous fraction comprising hydrocarbons containing the same number of carbon atoms which is sent to the dehydrogenation zone and into a heavier fraction which is recovered.

19. A process according to claim 3 comprising a prior fractionation step wherein the hydrocarbon feed is split into a homogeneous fraction comprising hydrocarbons containing the same number of carbon atoms which is sent to the dehydrogenation zone and into a heavier fraction which is recovered.

20. A process according to claims 8, wherein the hydrocarbon compound is isobutane.

* * * * *